US010321713B2

(12) United States Patent
Hopps et al.

(10) Patent No.: US 10,321,713 B2
(45) Date of Patent: Jun. 18, 2019

(54) HEATING SYSTEM AND METHOD OF HEATING FOR AN INHALER DEVICE

(71) Applicant: JT INTERNATIONAL S.A., Geneva (CH)

(72) Inventors: Jason Hopps, Coleraine Londonderry (GB); Philip Seeney, Cambridge (GB); Colin Turner, Cambridge (GB); Louise Oliver, Welwyn (GB)

(73) Assignee: JT International SA (CH)

(*) Notice: Subject to any disclaimer, the term of this patent is extended or adjusted under 35 U.S.C. 154(b) by 281 days.

(21) Appl. No.: 15/104,102

(22) PCT Filed: Nov. 26, 2014

(86) PCT No.: PCT/EP2014/075627
§ 371 (c)(1),
(2) Date: Jun. 13, 2016

(87) PCT Pub. No.: WO2015/086318
PCT Pub. Date: Jun. 18, 2015

(65) Prior Publication Data

US 2016/0331033 A1 Nov. 17, 2016

(30) Foreign Application Priority Data

Dec. 11, 2013 (EP) .................................... 13196732

(51) Int. Cl.
*A61M 15/06* (2006.01)
*H05B 1/02* (2006.01)
(Continued)

(52) U.S. Cl.
CPC ......... *A24F 47/008* (2013.01); *H05B 1/0297* (2013.01); *H05B 3/44* (2013.01)

(58) Field of Classification Search
None
See application file for complete search history.

(56) References Cited

U.S. PATENT DOCUMENTS 4,776,515 A * 10/1988 Michalchik ............... A61L 9/14 239/3
5,743,251 A * 4/1998 Howell ................ A61M 11/041 128/200.14
(Continued)

FOREIGN PATENT DOCUMENTS

EP 2327318 A1 6/2011
JP H1189551 A 4/1999
(Continued)

OTHER PUBLICATIONS

International Search Report for PCT/EP2014/075627 dated Mar. 12, 2015.

*Primary Examiner* — Thor S Campbell
(74) *Attorney, Agent, or Firm* — Lerner, David, Littenberg, Krumholz & Mentlik, LLP

(57) ABSTRACT

A heating system (3) for an inhaler device (1), such as an e-cigarette or a personal vaporizer, for generating an aerosol and/or a vapor (V) from a substance to be heated, especially a liquid or gel, the heating system (3) including: a first heating zone (5) configured to receive the substance to be heated from a supply reservoir (4), wherein at least one first heating element (14) is provided to pre-heat the substance in the first heating zone (5); and a second heating zone (16) configured to receive the preheated substance from the first heating zone (5), wherein at least one second heating element (19) is provided to heat the substance in the second heating zone (16).

19 Claims, 3 Drawing Sheets

(51) Int. Cl.
*H05B 3/44* (2006.01)
*A24F 47/00* (2006.01)

(56) References Cited

U.S. PATENT DOCUMENTS

| | | | | |
|---|---|---|---|---|
| 6,234,167 | B1 * | 5/2001 | Cox | A61M 15/0003 128/200.14 |
| 6,883,516 | B2 * | 4/2005 | Hindle | A61K 9/007 128/200.14 |
| 7,167,776 | B2 * | 1/2007 | Maharajh | F22B 1/28 219/483 |
| 9,084,440 | B2 | 6/2015 | Zuber et al. | |
| 9,271,528 | B2 * | 3/2016 | Liu | A24F 47/008 |
| 9,289,014 | B2 * | 3/2016 | Tucker | A24F 47/008 |
| 9,364,027 | B2 * | 6/2016 | Hon | A24F 47/002 |
| 9,918,496 | B2 * | 3/2018 | Kane | A24F 47/008 |
| 2002/0079309 | A1 | 6/2002 | Cox et al. | |
| 2003/0108342 | A1 * | 6/2003 | Sherwood | A61M 11/041 392/397 |
| 2003/0132219 | A1 * | 7/2003 | Cox | A61M 11/041 219/486 |
| 2006/0249144 | A1 | 11/2006 | DeHaan et al. | |
| 2011/0126848 | A1 | 6/2011 | Zuber et al. | |
| 2014/0000638 | A1 * | 1/2014 | Sebastian | A24F 47/008 131/328 |
| 2014/0261488 | A1 * | 9/2014 | Tucker | A24F 47/008 131/328 |
| 2014/0270726 | A1 * | 9/2014 | Egoyants | A24F 47/004 392/386 |
| 2014/0301721 | A1 | 10/2014 | Ruscio et al. | |
| 2014/0338680 | A1 | 11/2014 | Abramov et al. | |
| 2015/0272226 | A1 | 10/2015 | Zuber et al. | |

FOREIGN PATENT DOCUMENTS

| | | | |
|---|---|---|---|
| JP | 2004516101 | A | 6/2004 |
| JP | 2008539890 | A | 11/2008 |
| WO | 2013034460 | A1 | 3/2013 |
| WO | 2013060743 | A2 | 5/2013 |

* cited by examiner

HEATING SYSTEM AND METHOD OF HEATING FOR AN INHALER DEVICE

CROSS-REFERENCE TO RELATED APPLICATIONS

The present application is a national phase entry under 35 U.S.C. § 371 of International Application No. PCT/EP2014/075627, filed on Nov. 26, 2014, published in English, which claims priority from EP Patent Application No. 13196732.5, filed on Dec. 11, 2013, the disclosures of which are hereby incorporated herein by reference.

FIELD OF THE INVENTION

The present invention relates to an inhaler device, such as an electronic cigarette (e-cigarette), a personal vaporizer or an electronic vapor delivery system. More particularly, the invention relates to a heating system for such an inhaler device and a method of heating for generating an aerosol and/or a vapor from a substance to be heated in such a device.

BACKGROUND OF THE INVENTION

Inhaler devices of the above types, namely e-cigarettes and personal vaporizers and electronic vapor delivery systems, are proposed as an alternative to traditional smoking articles, such as cigarettes, cigarillos, cigars and the like. Typically, these inhaler devices are designed to heat a liquid solution or a gel to produce or generate an aerosol and/or a vapor to be inhaled by a user. This liquid is usually a solution of propylene glycol (PG) and/or vegetable glycerin (VG), and typically contains a flavorant or one or more concentrated flavors.

Despite the increasing demand for these inhaler devices and the growing market, efforts are still required to develop the performance of these devices, with a view to offering more efficient and improved products. For example, these efforts are directed to an improved aerosol and/or vapor generation, improved aerosol and/or vapor delivery, and more efficient use of energy in aerosol and/or vapor generation to improve the energy consumption, i.e. enhance the battery life of the device.

SUMMARY OF THE INVENTION

In view of the above, an object of the present invention is to provide an improved inhaler device, and more particularly an improved heating system and heating method for generating aerosol and/or vapor from a substance in an inhaler device.

According to one aspect, therefore, the invention provides a heating system for an inhaler device, such as an e-cigarette or a personal vaporizer, for generating an aerosol and/or vapor from a substance to be heated, especially a liquid or a gel, the heating system comprising:

- a first heating zone configured to receive the substance to be heated, wherein at least one first heating element is provided to preheat the substance in the first heating zone; and
- a second heating zone configured to receive the preheated substance from the first heating zone, wherein at least one second heating element is provided to heat the substance in the second heating zone.

In this way, the invention essentially provides a two-stage heating system for the inhaler device. An initial heating or "preheating" of the substance (e.g. liquid or gel) occurs in the first heating zone. Here the substance may be subject to pressurization, possibly even boil and partially vaporize, and will typically undergo a thermal expansion. The thermal expansion may generate a localized pressure increase in the first heating zone, which then forces or drives the substance under pressure towards the second heating zone. In such a case, the substance may be comprised of an aerosol, droplets, and/or suspension of the liquid solution or gel to be heated and/or a vapor thereof. Thus, in the second heating zone, the degree of heating required to carry out full vaporization of the substance can be achieved both quickly and efficiently. The first and second heating zones typically comprise or are formed by regions or spaces which are physically distinct and separate from one another. Nevertheless, the first and second heating zones are usually designed to be in fluid communication with one another.

In a preferred embodiment of the invention, the first heating zone comprises at least one first heating cavity. Thus, the at least one first heating cavity is configured to receive the substance to be heated, e.g. from a supply reservoir. In a particularly preferred embodiment, the first heating zone comprises a single cavity and the at least one first heating element may be provided or arranged in that first heating cavity. Similarly, the second heating zone comprises at least one second heating cavity configured to receive the preheated substance from the first heating zone. In one embodiment, the second heating zone comprises a plurality of second heating cavities, and a second heating element may be provided or arranged in each of the second heating cavities.

Thus, in a preferred embodiment of the invention, a heating system for an inhaler device, such as an e-cigarette or a personal vaporizer, is provided for generating an aerosol and/or a vapor from a substance to be heated, especially a liquid or a gel, the heating system comprising:

- at least one first heating cavity configured to receive the substance to be heated from a substance supply, wherein at least one first heating element is provided to preheat the substance in the first heating cavity; and
- at least one second heating cavity configured to receive the preheated substance from the first heating cavity, wherein at least one second heating element is provided to heat the substance in the second heating cavity.

In a preferred embodiment, the second heating zone is in fluid communication with the first heating zone, preferably via one or more grooves or channels. Where the second heating zone comprises a number of second heating cavities, the fluid communication with the first heating zone may then be via a plurality of grooves or channels; i.e. at least one groove or channel per second heating cavity. The preheated substance is therefore able to migrate from the first heating zone to the second heating zone after preheating. That is, the preheated substance may begin to boil or vaporize in the first heating zone and expands (e.g. as vapor, thermally expanding liquid, or discrete liquid droplets) along the one or more grooves or channels into the second heating zone or cavities.

In a preferred embodiment, the heating system includes a body member or support body and the first heating zone or cavity may be formed in or around a periphery of this support body. The support body is preferably generally cylindrical in shape and the first heating zone or cavity is preferably generally annular in shape around a periphery of the support body. In a similar manner, the at least one second heating cavity may be formed in or around a periphery of the support body. Where a plurality of second cavities is provided, for example, each second heating cavity may extend axially towards an end face of the support body. As noted above, the first and second heating elements are preferably respectively located in the first and second heating cavities. Accordingly, the first and second heating elements may be supported on the support body, which preferably comprises an electrically insulating material. As the first and second heating cavities are typically small and precisely dimensioned, the support body is preferably also be formed of a material that may be machined or manufactured with precision. A ceramic material is therefore preferred for the support body, as it may satisfy both of these requirements, as well as being very temperature resistant. Other materials, such as polymer plastics, silicates, or similar materials may also be contemplated, however.

In a particularly preferred embodiment, each of the first and second heating elements may comprise an electrical resistance element, such as a wire, ribbon, strip, foil, or conductive coating for Joule heating or resistance heating. Such a wire or coil may extend through the first and/or second heating cavities. In the case of a foil, however, this may be provided as a film deposit or lining on a surface of the first or second heating cavities. The heating elements preferably comprise a material selected from the group of Nichrome 80/20, Cupronickel (CuNi) alloys, Kanthal (FeCrAl), and molybdenum silicide ($MoSi_2$). The first and/or second heating elements are preferably powered by an electrical supply, such as a battery, in the inhaler device.

In a preferred embodiment, each second heating cavity forms or provides a chamber for the heated substance as it expands and vaporizes. That is, the substance (e.g. liquid or gel) is further vaporized in the second heating zone and undergoes a large volumetric expansion during the phase change to gas. Each second heating cavity preferably also communicates with at least one nozzle for delivery of the vapor and/or aerosol produced in the second heating zone to a mouthpiece of the inhaler device.

In a preferred embodiment, the heating system includes a housing that accommodates the support body and encloses the first and second heating zones together with a chamber that forms a supply reservoir for the substance to be heated. A plug or baffle member may separate the supply reservoir from the first heating zone, and yet provide fluid communication there-between.

In a preferred embodiment, the first heating zone or cavity is configured to receive the substance to be heated (e.g. a liquid or gel) from the supply reservoir via a feed mechanism. The feed mechanism may, for example, include one or more of capillary action and pressure bias through the fluid communication. The capillary action may be created by providing narrow channels or passages which communicate from the supply reservoir to the first heating zone or cavity. These could, for example, be provided in the plug or baffle member and/or in a side wall of the housing, e.g. adjacent the plug or baffle member. On the other hand, a pressure bias could be created by applying pressure to the liquid or gel substance stored in the supply reservoir, such that it is biased from the reservoir towards the first heating zone or cavity. Alternatively, or in addition, the supply reservoir may be flexible or collapsible for applying a pressure bias, and/or may include a vent such that suction and capillary action create a pressure bias between the reservoir and the first heating zone promoting migration of the substance to the first heating zone(s). Further, the feed mechanism may be configured to vary a feed rate of the substance from the supply reservoir to the first heating zone or cavity. In this regard, the plug member or baffle member may be deformable to modify the one or more channels or passages providing the fluid communication with the first heating zone or cavity, thereby affecting the feed rate. In this way, the feed mechanism of the system may include a valve mechanism to regulate the feed rate of the substance. The feed rate may be set or adjusted by a user to match or suit an inhalation profile of the user. A valve mechanism could then be used to shut-off transfer or conveyance of the liquid or gel from the supply reservoir to the first heating zone when the inhaler device is not in use, e.g. when it is switched off.

In a preferred embodiment, the housing that accommodates the support body includes one or more air inlets, such that air may be drawn in and mixed with the vaporized substance as it is transformed to a vapour. The one or more air inlets may direct air into the second heating zone, or may alternatively be provided either upstream and/or downstream of the second heating zone. Thus, in a particular embodiment, the housing may include a plurality of holes extending (e.g. radially) through a side wall of the housing into each of the plurality of second heating cavities. The one or more air inlets or the inlet holes may serve to provide a balancing air-flow; i.e. to create a desired air-flow resistance for a user when the system is incorporated in an inhaler device. Preferably, the one or more air inlets can be selectively changed or adjusted by a user, e.g. by modifying an air inlet size, to regulate a mix of inlet air and the aerosol and/or vapour to be inhaled and to modify the flow resistance of the device.

According to a further aspect, the present invention provides an inhaler device, especially an electronic cigarette or a personal vaporizer, for generating an aerosol and/or vapor from a substance to be heated, such as a liquid or gel, wherein the inhaler device includes a heating system according to any one of the embodiments described above.

According to yet another aspect, the invention provides a method of heating a substance, especially a liquid or gel, in an inhaler device, such as an e-cigarette or a personal vaporizer, the method comprising:

conveying the substance to be heated from a supply reservoir to a first heating zone;
preheating the substance in the first heating zone;
conveying the preheated substance from the first heating zone to a second heating zone; and
heating the substance in the second heating zone to form a vapor, which then typically condenses to form an aerosol.

In a preferred embodiment of the invention, the step of preheating the substance to be heated in the first heating zone and/or the step of heating that substance in the second heating zone is performed by one or more electrical heating elements. As noted above, each of the first and second heating elements may respectively comprise an electrical resistance element, such as a wire, ribbon, strip, or foil, for Joule heating or resistance heating and are desirably powered by an electrical supply, such as a battery, in the inhaler device.

In a preferred embodiment the step of conveying the substance to be heated from a supply reservoir to a first heating zone includes at least one of capillary action and pressure bias, as discussed in detail above. Further, the step of conveying the preheated substance from the first heating zone to the second heating zone desirably includes thermal expansion and/or capillary action, as also discussed above.

In a preferred embodiment, each of the preheating and heating steps may be carried out periodically or sequentially. That is, each of the heating zones may be activated or powered in an alternating or pulsed manner in specific or predetermined activation intervals or periods. For example, an activation period of 50 msec could be applied to the first heating zone (e.g. to power or activate the first heating element(s) for this period), followed by an activation period of 50 msec for the second heating zone. Such pulsed activation of the two heating zones can provide improved energy consumption.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which.

DETAILED DESCRIPTION OF SOME EMBODIMENTS OF THE INVENTION

Figure 1:
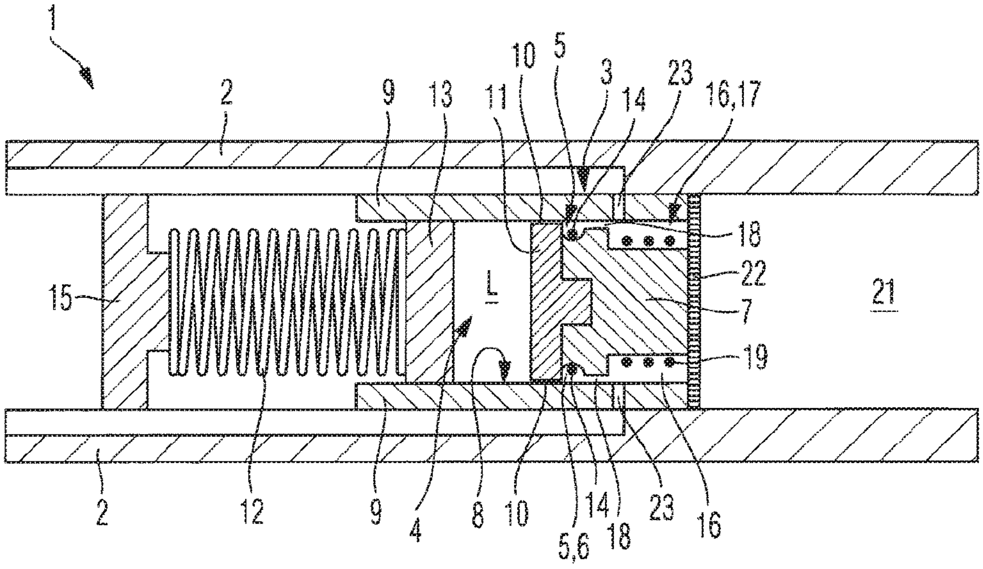
FIG. 1 is a schematic cross-sectioned side view of a heating system in an inhaler device according to an embodiment of the invention.

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

With reference to FIGS. 1 to 4 of the drawings, a part of an inhaler device 1 embodied as an electronic cigarette (also known as an "e-cigarette") is represented schematically. This inhaler device 1 includes a casing 2 provided in the form of a generally cylindrical sleeve, which accommodates a heating system 3 according to the invention. The heating system 3 is designed for heating a liquid solution or gel L supplied from a reservoir 4 in the inhaler device 1 to generate an aerosol and/or vapor V for inhalation by a user as a substitute for smoking traditional cigarettes. To this end, the liquid L may include a solution of propylene glycol, vegetable glycerin, a flavorant, and/or one or more flavours.

The heating system 3 of this embodiment provides two-step or two-stage heating of the liquid L to generate or produce the aerosol and/or vapor V for inhalation. In particular, the heating system 3 includes a first heating zone 5 formed by an annular cavity 6 around a periphery of a generally cylindrical body member 7. In other words, this annular cavity 6 formed between the body member 7 and a side wall 8 of a generally cylindrical housing 9 accommodating the heating system 3 forms the first heating cavity. This first heating zone 5 or cavity 6 is configured to receive the liquid L from the adjacent supply reservoir 4 via fine channels or passages 10 formed between an outer rim or periphery of a plug member 11 and the side wall 8 of the housing 9. In particular, the heating system 3 has a feed mechanism for delivering or conveying the liquid L from the supply reservoir 4 to the first heating zone 5 or first heating cavity 6. In the present example, the feed mechanism comprises a combination of capillary action through the fine channels or passages 10 and pressure applied to the liquid L in the reservoir 4 via a spring 12 which acts on a movable piston 13. However, a feed mechanism may also be contemplated that comprises only capillary action or only a pressurizing means without affecting the working principles of the present invention.

Figure 2:
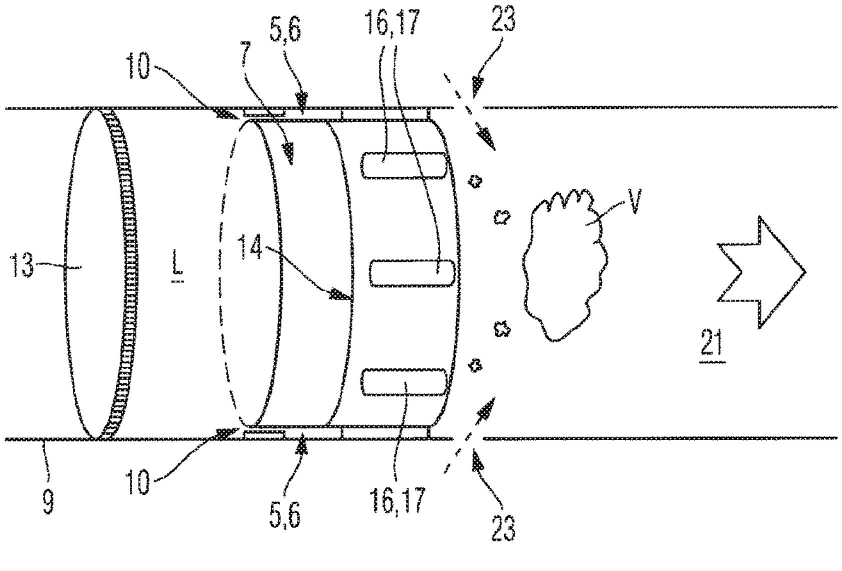
FIG. 2 is a schematic perspective view of the heating system in the inhaler device of FIG. 1.
Figure 3:
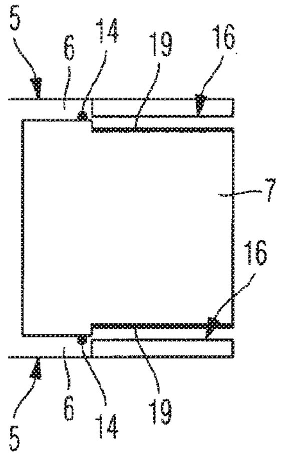
FIG. 3 is a schematic cross-sectioned side view of part of a heating system according to an embodiment of the invention.
Figure 4:
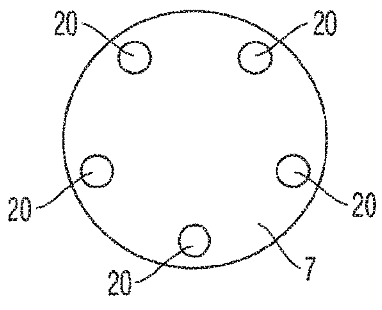
FIG. 4 is a schematic end view of the heating system in FIG. 3.

As can be seen in FIGS. 1 and 2, the annular first heating cavity 6 includes a heating element 14 provided in this case in the form of a Nichrome 80/20 wire which extends around and is supported by the body member 7 and is in intimate contact with the liquid L as it enters this first heating zone 5 from the supply reservoir 4. This first heating element or wire 14 is provided with electrical energy from a battery 15 and is thereby heated when the inhaler device 1 is switched "on" or activated to effect a preheating of the liquid L in the first heating zone 5. As the liquid L in the first heating zone 5 undergoes initial heating, it may begin to boil or at least become pressurized, such that it is transferred or conveyed to a second heating zone 16 by thermal expansion and under the influence of an influx of new liquid L into the first heating zone 5 or first cavity 6 from the supply reservoir. Thus, the liquid L is already preheated as it enters the second heating zone 16 of the heating system 3 of the invention.

In this embodiment, the second heating zone 16 comprises a number of separate cavities 17 which are again formed in a periphery of the body member 7 towards an end thereof. These second heating cavities 19 are arranged spaced apart around the body member 7 and extend generally parallel to a central axis thereof. In this way, the plurality of second heating cavities 17 collectively form the second heating zone 16 and each is configured to receive the preheated liquid L from the first heating zone 5 via channels or grooves 18 again formed in the periphery of the body member 7.

Each of the second heating cavities 17 also includes a second heating element 19 for electrically heating the liquid L that enters the second heating zone. Each of the second heating elements 19 may be formed from a Nichrome 80/20 wire, as with the first heating element 14. Alternatively, however, these second heating elements may comprise a conducting foil, e.g. of molybdenum silicide ($MoSi_2$), which may be deposited as a film over a surface of each second cavity 17. In any case, the second heating elements 19 further heat the preheated liquid L to effect its full vaporization. Each second heating cavity 17 therefore forms an expansion chamber into which gas formed through the vaporization of the liquid L may expand. For this reason, each of the second heating cavities 17 may terminate in or communicates with a nozzle 20 at an end face of body member 7, through which the vapor V is emitted into a channel 21 from which the user may inhale that aerosol and/or vapour V via a mouthpiece (not shown) of the inhaler device 1. Optionally, a foil 22 with multiple micro-openings or holes may be provided over an end region of the body member 7 and housing 9 facing the channel 21. This foil 22 may, for example, form a filter membrane for the aerosol and vapour V emitted from the heating system 3. At the same time, the foil 22 may also provide air-flow resistance, whereby a pressure difference develops across the foil array and the gas emitted there-through undergoes an expansion and vapour-phase cooling to form inhalable aerosol droplets.

As is also apparent from FIG. 1 of the drawings, radial air inlets 23 may be provided through the side wall 8 of the housing 9 into each of the second heating cavities 17 to enable the influx and mixture of air with the vapour V in the second heating zone 16. This may assist with ensuring that a proper flavour or concentration balance is provided in the aerosol and/or vapor V produced. Furthermore, the radial inlets 23 may be used to balance the airflow through the device to provide a desired airflow resistance or "inhalation feel" for the user. Also, this may assist to cool the aerosol or vapour V before it reaches the user via a mouthpiece of the inhaler device 1. It will be noted that air inlets may also be provided downstream of the nozzles 20, e.g. in the channel 21, to balance or control the flow. With reference to FIG. 2, for example, it will be seen that air inlets 23 may be provided opening radially into the channel 21 downstream of the second heating zone 16, instead of (or in addition to) into the second heating cavities 17 directly.

It will be noted that cylindrical body member 7 is desirably comprised of a ceramic material that is pre-machined or fabricated to form the respective first and second heating cavities 6, 17 in its periphery, together with the channels, grooves and/or passages 10, 18 which provide the fluid communication between the supply reservoir 4 and first heating zone 5, and between the first and second heating zones 5, 16, respectively. As the ceramic body member 7 also supports the first and second electrical heating elements 14, 17, the electrical insulating properties of the ceramic material are relevant to a desired and proper functioning of this heating system 3.

It will also be noted that the heating system 3 shown in this embodiment may optionally be provided in a cartridge designed to be inserted into the casing 2 of the inhaler device 1. That is, the housing 9 incorporating the supply reservoir 4 of the liquid L and the heating system 3 described above may be provided as a replaceable (e.g. disposable) cartridge, so that once the supply reservoir 4 of the liquid L to be heated is depleted or exhausted, that cartridge may be removed and a replacement cartridge may then be inserted into the casing 2 of the inhaler device 1 in its place. The depleted cartridge could then either be re-filled with liquid L to be used again or simply disposed of.

With reference now to FIGS. 5 to 9 of the drawings, a part of an inhaler device 1 again embodied as an electronic cigarette (e-cigarette) is shown schematically. As before, the inhaler device 1 includes a casing 2 which is a generally cylindrical sleeve and accommodates a heating system 3 according to yet another embodiment of this invention. The heating system 3 is again designed for heating a liquid solution or gel L that is supplied from a reservoir 4 in inhaler device 1 to generate an aerosol and/or a vapor V for inhalation by a user as a substitute for smoking traditional cigarettes. To this end, the liquid L is typically provided as a solution of propylene glycol, vegetable glycerin, a flavorant, and/or flavours.

Figure 5:
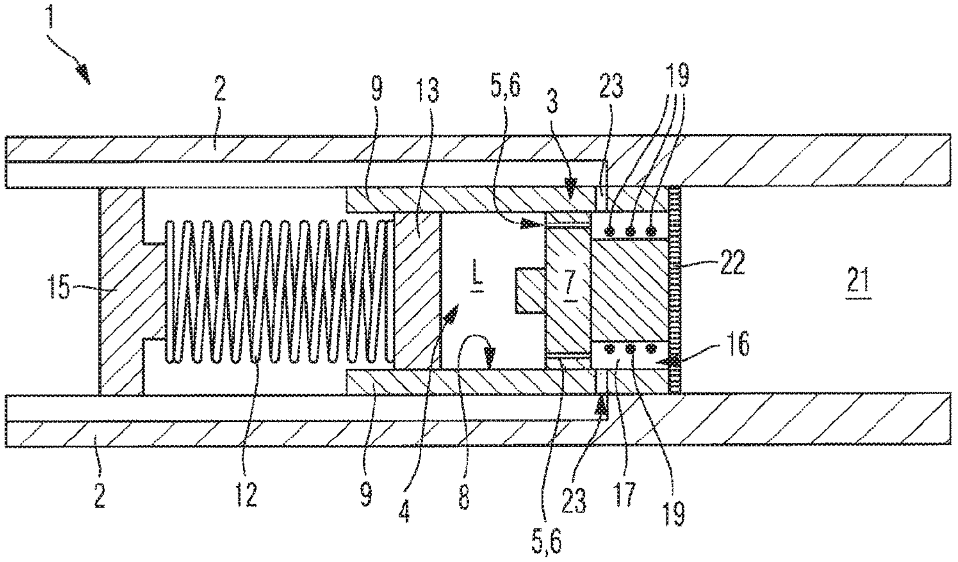
FIG. 5 is a schematic cross-sectioned side view of a heating system in an inhaler device according to another embodiment of the invention.
Figure 6:
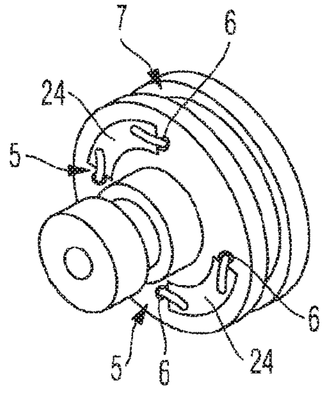
FIG. 6 is a schematic perspective view of a part of a heating system according to the embodiment of the invention in FIG. 5.
Figure 7:
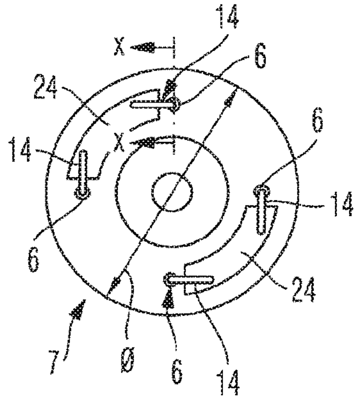
FIG. 7 is a schematic end view of that part of the heating system shown in FIG. 6.

The heating system 3 of this embodiment provides a two-step or two-stage heating of the liquid L to generate or produce the aerosol and/or vapor V for inhalation. In particular, with reference also to FIGS. 6 and 7 of the drawings, the heating system 3 includes a first heating zone 5 comprising a plurality first heating cavities 6 provided as supply channels formed in and through a body member 7, and a number of first heating elements 14 in the form of metal wires which extend through each of the supply channels 6. As can be seen in FIGS. 5 to 7, the body member 7 may have a generally round or cylindrical shape and is optionally accommodated within a generally cylindrical housing 9.

As seen in drawing FIGS. 6 and 7, the supply channels 6 are provided as fine bores or passages having a diameter in the range of about 0.1 mm to 2.0 mm, preferably in the range of 0.1 mm to 1.0 mm (e.g. a diameter of about 0.5 mm), which are drilled to extend generally axially through the body member 7 for conveying the liquid solution L from a supply reservoir 4 by capillary action, i.e. by surface tension forces within the channels 6. The body member 7 in this case preferably has a diameter $\varphi$ of about 12 mm. The capillary channels 6 of the first heating zone 5 are configured to receive the liquid L from the adjacent supply reservoir 4 via direct contact ensured by a feed mechanism for delivering the liquid L in the supply reservoir 4 to the first heating zone 5. In this embodiment, as before, the feed mechanism applies pressure to the liquid L in the reservoir 4 via a spring 12 which acts on a movable piston 13.

Figure 8:
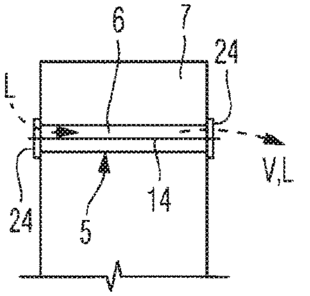
FIG. 8 is a schematic partial cross-sectional view in the direction of arrows X-X in FIG. 7.

The heating elements 14 arranged in the supply channels 6 in this case are comprised of Nichrome 80/20 wires which may be joined or interconnected over a face of the body member 7 by conductive bridges 24. Furthermore, as can be seen in FIG. 8, these wire heating elements 14 are preferably arranged such that they are not in contact with an internal surface of the channels 6, but rather extend freely (i.e. spaced from the internal surfaces) substantially centrally and/or along a longitudinal axis of the channels 6. This can advantageously limit or minimise the formation of deposits and residues in a channel 6 from the liquid L being heated. As an alternative, however, the first heating elements 14 could also comprise conductive foil, e.g. molybdenum silicide ($MoSi_2$), deposited as a film over a surface of each channel 6.

Thus, the bridges 24 interconnecting the heating elements 14 conduct electric current to each of the wires 14 that extend through the capillary bores 6, but do not themselves perform any heating. The heating wires 14 are in intimate contact with the liquid L as it is passes from the supply reservoir 4 through and along the supply channels 6 by or under capillary action. These first heating elements or wires 14 are provided with electrical energy from a battery 15 and are thereby heated when the inhaler device 1 is electrically activated or switched "on" to effect a preheating of the liquid L in the first heating zone 5. As the liquid L in the first heating zone 5 undergoes initial heating, it may begin to boil or at least expand and become pressurized, such that it is conveyed or transferred by thermal expansion and by capillary action to a second heating zone 16, as well as by the influence of an influx of new liquid L into the first heating zone 5 or channels 6 from the reservoir 4. In this way, the liquid L is already preheated as it emerges from the channels 6 into a second heating cavity or chamber 17, which forms the main or second heating zone 16 of the inventive heating system 3.

Thus, in this embodiment, the second heating zone 16 includes a heating cavity 17 and at least one second heating element 19 for electrically heating the liquid L when it enters the second heating zone. The second heating element 19 in this example comprises a wire coil and, as with the first heating elements 14, may again be formed from Nichrome 80/20 wire. In any case, the second heating element 19 further heats the preheated liquid L to effect its full vaporization in the cavity or chamber 17, in which gas formed by the vaporization of the liquid L may expand. For this reason, the second heating cavity 17 may optionally terminate in or communicate with a nozzle 20 at an end face of body member 7, through which the vapor V is emitted into a vapor channel 21 and from which the user may inhale that aerosol and/or vapour V via a mouthpiece (not shown) of the inhaler device 1. Optionally, a foil 22 with multiple micro-openings or holes may be provided over an end region of the body member 7 and housing 9 facing the vapor channel 21. This foil 22 may, for example, form a filter membrane for the aerosol and vapor V emitted from the heating system 3. At the same time, the foil 22 may provide air-flow resistance, whereby a pressure difference develops across the array and the gas emitted undergoes an expansion and vapour-phase cooling to form inhalable aerosol droplets.

Figure 9:
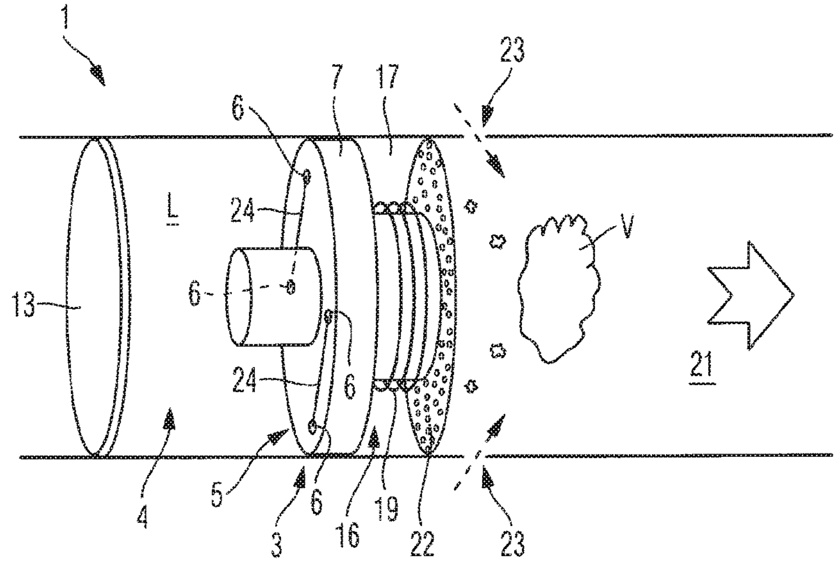
FIG. 9 is a schematic perspective view of the heating system in the inhaler device of FIG. 5.

As is apparent from drawing FIG. 5, radial air inlets 23 may be provided through side walls 8 of the housing 9 into the second heating cavity 17 to enable the influx and mixture of air with the vapour V in the second heating zone 16. This may assist with ensuring that a proper flavour or concentration balance is provided in the aerosol and/or vapor V produced. Furthermore, the radial inlets 23 may be used to balance the airflow through the device and to provide a desired airflow resistance or "inhalation feel" for the user. This may also assist to cool the aerosol or vapour V before it reaches the user via a mouthpiece of the inhaler device 1. It will be noted that air inlets may also be provided downstream of any such nozzles 20, e.g. in the vapor channel 21, to balance or control the flow. With reference to FIG. 9, for example, air inlets 23 may be provided opening radially into the vapor channel 21 downstream of the second heating zone 16, instead of (or in addition to) air inlets into the second heating cavity 17 directly.

It will be noted that cylindrical body member 7 is desirably comprised of a ceramic material that is pre-machined or fabricated to form the supply channels 6 providing the fluid communication between the supply reservoir 4 and the second heating zone 16. As the ceramic body member 7 also supports the first and second electrical heating elements 14, 19, the electrical insulating properties of the ceramic material are relevant to a desired and proper functioning of this heating system 3.

It will also be noted that the heating system 3 shown in this embodiment may optionally be provided in a cartridge designed to be inserted into the casing 2 of the inhaler device 1. That is, the housing 9 incorporating the supply reservoir 4 of the liquid L and the heating system 3 described above may be provided as a replaceable (e.g. disposable) cartridge, so that once the supply reservoir 4 of the liquid L to be heated is depleted or exhausted, that cartridge may be removed and a replacement cartridge may then be inserted into the casing 2 of the inhaler device 1 in its place. The depleted cartridge could then either be re-filled with liquid L to be used again or simply disposed of.

Although specific embodiments of the invention have been illustrated and described herein, it will be appreciated by those of ordinary skill in the art that a variety of alternate and/or equivalent implementations exist. It should be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

Also, it will be appreciated that in this document, the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

The invention claimed is:

1. A heating system for an inhaler device for generating an aerosol or a vapor from a substance to be heated, the heating system comprising:

a body member having an outer peripheral surface facing an inner surface of a housing of the inhaler device;

a first heating zone configured to receive the substance to be heated from a supply reservoir, wherein at least a first heating element is provided to preheat the substance in the first heating zone, the first heating zone comprising at least one first heating cavity extending into the body member and configured to receive the substance to be heated from a supply reservoir that is separated from the first heating cavity; and a second heating zone configured to receive the preheated substance from the first heating zone, wherein at least one second heating element is provided to heat the substance in the second heating zone, the second heating zone comprising at least one second heating cavity extending into the body member, the second cavity being partially separated from the first heating cavity by a portion of the body member.

2. The heating system according to claim 1, wherein the second heating zone is in fluid communication with the first heating zone via one or more grooves or channels for migration of the preheated substance from the first heating zone to the second heating zone after preheating.

3. The heating system according to claim 1, wherein the first heating zone is formed in or around a periphery of a body member, and wherein the first heating zone is generally annular in shape.

4. The heating system according to claim 1, wherein the second heating zone is formed in or around a periphery of a body member; wherein the second heating zone extends axially of the body member.

5. The heating system according to claim 1, wherein the second heating zone includes a number of second heating cavities, and wherein each second heating cavity forms or provides an expansion chamber for the substance as it vaporizes.

6. The heating system according to claim 1, wherein each first heating element is located in the first heating zone and each second heating element is located in the second heating zone; wherein the first and second heating elements are respectively supported on a body member.

7. The heating system according to claim 1, further comprising the housing that accommodates the first and second heating zones together with a chamber that forms a supply reservoir for the substance to be heated; wherein a plug or baffle member separates the supply reservoir from the first heating zone and provides fluid communication there-between.

8. The heating system according to claim 7, wherein the first heating zone is configured to receive the substance to be heated from the supply reservoir via a feed mechanism; wherein the feed mechanism includes one or more of capillary action and fluid pressure through the fluid communication.

9. A heating system according to claim 8, wherein the feed mechanism is configured to vary a feed rate of the substance from the supply reservoir to the first heating cavity, wherein the plug or baffle member is deformable to modify the feed rate.

10. An inhaler device for producing aerosol or vapor from a substance to be heated, wherein the inhaler device includes a heating system which comprises:

a body member having an outer peripheral surface facing an inner surface of a housing of the inhaler device;

a first heating zone configured to receive the substance to be heated from a supply reservoir, wherein at least a first heating element is provided to preheat the substance in the first heating zone, the first heating zone comprising at least one first heating cavity extending into the body member and configured to receive the substance to be heated from a supply reservoir that is separated from the first heating cavity; and a second heating zone configured to receive the preheated substance from the first heating zone, wherein at least one second heating element is provided to heat the substance in the second heating zone, the second heating zone comprising at least one second heating cavity extending into the body member, the second cavity being partially separated from the first heating cavity by a portion of the body member.

11. The inhaler device according to claim 10, wherein the inhaler device is an e-cigarette or a personal vaporizer.

12. A method of heating a substance in an inhaler device, the method comprising:

providing a body member having an outer peripheral surface facing an inner surface of a housing of the inhaler device;

conveying the substance to be heated from a supply reservoir to a first heating zone, the first heating zone comprising at least one first heating cavity extending into the body member, the supply reservoir being separated from the first heating cavity;

preheating the substance in the first heating zone;

conveying the preheated substance from the first heating zone to a second heating zone, the second heating zone comprising at least one second heating cavity extending into the body member, the second cavity being partially separated from the first heating cavity by a portion of the body member; and heating the substance in the second heating zone to form a vapor.

13. The method according to claim 12, wherein preheating the substance is performed by one or more electrical heating element.

14. The method according to claim 12, wherein conveying the substance to be heated from a supply reservoir to the first heating zone includes at least one of capillary action and fluid pressure.

15. The method according to claim 12, wherein preheating the substance in the first heating zone is carried out on a periodical or intermittent basis.

16. The method according to claim 12, wherein heating the substance is performed by one or more electrical heating elements.

17. The method according to claim 12, wherein conveying the preheated substance from the first heating zone to the second heating zone includes at least one of capillary action and fluid pressure.

18. The method according to claim 12, wherein heating the substance in the second heating zone is carried out on a periodical or intermittent basis.

19. The method according to claim 12, wherein the substance is a liquid or a gel.

* * * * *